United States Patent [19]

Szabo

[11] Patent Number: 5,223,521
[45] Date of Patent: Jun. 29, 1993

[54] PYRAZOLE AND THIOZOLE DERIVATIVES FOR TREATMENT OF GASTROINTESTINAL ULCER DISEASE

[75] Inventor: Sandor Szabo, Brookline, Mass.

[73] Assignee: Brigham and Women's Hospital, Boston, Mass.

[21] Appl. No.: 666,391

[22] Filed: Mar. 8, 1991

[51] Int. Cl.$^5$ ............... A61K 31/415; A61K 31/425
[52] U.S. Cl. ................................ 514/365; 514/406; 514/407; 514/926; 514/927
[58] Field of Search ............... 514/365, 406, 407, 926, 514/927

[56] References Cited

U.S. PATENT DOCUMENTS

| | | | |
|---|---|---|---|
| 4,391,814 | 7/1983 | Vorbrüggen | 513/406 X |
| 4,432,983 | 2/1984 | Riley et al. | 514/304 |
| 4,497,810 | 2/1985 | Hoffman | 514/222.5 |

OTHER PUBLICATIONS

Brooks, F. P. in *Peptic Ulcer Disease: Contemporary Issues in Gastroenterology*, Brooks, F. P., et al., eds., Churchill-Livingston, New York, pp. 45–149 (1985).
Dupuy et al., *Digestion* 31:165, Abstract 65 (1985).
Dupuy et al., *Gastroenterology* 91(4):966–974 (1986).
Ezer, E., *Digestion* 31:168, Abstract 74 (1985).
Friedman, M., *The Chemistry and Biochemistry of the Sulfhydryl Groups in Amino Acids*, Oxford: Pergamon, pp. 25–51 (1973).
Garner, A., Scand. J. Gastroenterol. 21, Suppl. 125:203–210 (1986).
Hauser et al., *Faseb J.* 2(5):1052, Abstract 4395 (1988).
Lanza et al., *The American Journal of Gastroenterology* 80(10):767–769 (1985).
Leung et al., *Gastroenterology* 88:1948–1953 (1985).
Lorenz et al., *Lancet* 1:1261–1264 (1984).
Miller, T. A., *Amer. J. Physiol.* 245:G601–G623 (1983).
Mizui et al., *Japan J. Pharmacol* 33:939–945 (1983).
Sessa et al., *Alcoholism: Clinical and Experimental Research* 8(2):185–190 (1984).
Sutton et al., *Gastroenterology* 69(1):166–174 (1975).
Szabo, S., *Scand. J. Gastroenterol.* 23:1–6 (1988).
Szabo, S., *Laboratory Investigation* 51(2):121–147 (1984).
Szabo et al., *Gastroenterology* 88(1)Part 2, pp. 228–236 (1985).
Szabo, S., Klin Wochenschr. 64, Suppl. VII, pp. 116–122 (1986).
Szabo, S., *Science* 214:200–202 (1981).

*Primary Examiner*—Leonard Schenkman
*Attorney, Agent, or Firm*—Sterne, Kessler, Goldstein & Fox

[57] ABSTRACT

The invention relates to a method of preventing or treating gastrointestinal ulcer disease and microvascular injury in a mammal comprising administering to said mammal a pyrazole derivative alone or in combination with an ulcerogenic agent. The invention further relates to pharmaceutical compositions comprising a pyrazole derivative in combination with an ulcerogenic therapeutic agent to inhibit or prevent the ulcerogenic effect of that agent.

35 Claims, No Drawings

PYRAZOLE AND THIOZOLE DERIVATIVES FOR TREATMENT OF GASTROINTESTINAL ULCER DISEASE

BACKGROUND OF THE INVENTION

Field of the Invention

The invention relates to a method of treating gastrointestinal ulcer disease in a mammal comprising administering to said mammal a pyrazole derivative. The invention further relates to a pharmaceutical composition comprising a pyrazole derivative in combination with a therapeutic agent which is itself ulcerogenic. The invention further relates to a method of treating microvascular injury in a mammal comprising administering to said mammal a pyrazole derivative.

Description of the Background Art

Nonspecific ulcers in the upper gastrointestinal tract (stomach and duodenum), commonly but inaccurately referred to as "peptic ulcers," affect about 10% of the population of the United States at least once in a lifetime. *Gastroenterology* 69:166-174 (1975).

Drug-induced (iatrogenic) ulcers are even more common. A large proportion of chronic users of aspirin and nonsteroidal anti-inflammatory drugs (e.g., patients with rheumatoid arthritis and osteoarthritis, and healthy people seeking prevention of disease) are affected by drug-induced ulcers in a dose- and time-dependent manner. Lanza, F. L., et al., *Amer. J. Gastroenterol.* 80:767-769 (1985); Lorenz, R. L., et al., *Lancet* 1:1261-1264 (1984). Ulcer inducing agents are also referred to as "ulcerogenic" agents.

"Ulcer disease," which is a more accurate designation than "peptic ulcer," is considered a mass disorder because, just as in cardiovascular diseases and cancer, it affects a large segment of the population. Similarly, the pathophysiology of ulcer disease is poorly understood. It is now clear that ulcer disease is a complex disorder that is multifactorial or pluricausal in origin. (Brooks, F. P., in *Peptic Ulcer Disease: Contemporary Issues in Gastroenterology*, Brooks, F. P., et al., eds., Churchill-Livingston, New York, 1985, 145-151); Szabo, S., *Laboratory Investigations* 51:121-147 (1984).

The multifactorial etiology and pathogenesis imply that it is unrealistic to expect a complete healing or a preventive effect from highly specific drugs that affect only one component in this complex chain of events. Thus, it is not surprising that after cessation of treatment with even the most potent of the current antisecretory agents, the $H_2$ receptor antagonists such as cimetidine, the recurrence rate of chronic duodenal ulcers is 40-60% a year. Thomas, J. M., et al., *Clin. Gastroenterol.* 13:501-541 (1984).

Novel drugs which affect more than one element in the pathogenesis of ulcer disease are thus realistically expected to have a more profound effect on ulcer healing and recurrence than presently available antiulcer drugs. "Future research must address the different etiologies of gastric and duodenal ulcers and other acid-peptic conditions, as well as attempting to cure the disease, rather than simply heal the ulcer." Garner, A., *Scand. J. Gastroenterol.* 21, Suppl. 125:203-210 (1986).

Pyrazole is a known inhibitor of the enzyme alcohol dehydrogenase (ADH) in the gastrointestine. Sessa et al., *Alcoholism: Clinical and Experimental Research* 8:158 (1984). The methods for producing pyrazole are reported in V. Pechman, *Ber.* 31:2950 (1898). Pyrazole is also known to be a histamine $H_2$ receptor antagonist and has been used as a substituent in antisecretory agents which function by antagonizing histamine $H_2$ receptors. U.S. Pat. No. 4,497,810, Hoffman Jr., and U.S. Pat. No. 4,432,983, Riley et al.

"Gastric cytoprotection", a recently developed concept in ulcer prevention, is focused on the prevention of acute mucosal lesions without decreasing gastric acidity. Based on this concept, new compounds have been developed to provide protection for the gastric mucosa. As originally defined, gastric "cytoprotection" or "gastroprotection" referred to several specific modalities used to prevent hemorrhagic gastric erosions without inhibiting acid secretion. Examples of these specific modalities include: the prostaglandins; sulfhydryl group-containing drugs that protect animals from ethanol-induced gastric erosions; and certain other agents. Miller, T. A., *Amer. J. Physiol.* 245:G601-623 (1983); Szabo, S., et al., *Science* 214:200-202 (1981).

Early vascular damage is an important event in the process leading to hemorrhagic mucosal injury, and vascular lesions have been shown to be early pathogenetic factors in gastric hemorrhagic erosions (Leung et al., *Gastroenterology* 88:1948-1953 (1985); Szabo et al., *Gastroenterology* 88:228-236 (1985)). Therefore, the prevention of chemically induced vascular endothelial damage in the gastric mucosa may be a major mechanism of gastric cytoprotection.

Additional evidence of the involvement of sulfhydryl groups in gastric cytoprotection is provided by reports that the protection afforded by prostaglandins and sulfhydryls, diethylmaleate, polyamines, and sodium salicylate can be counteracted by the irreversible sulfhydryl blocker, N-ethylmaleimide. Szabo, S., et al., *Science* 214:200-202 (1981); Szabo, S., *Klin Wochenschr.* 64, Suppl. VII, 116-122 (1986); Dupuy, D., et al., *Digestion* 31:165 (1985); Mizui, T., et al., *Japan J. Pharmacol.* 33:939-945 (1983); Ezer, E., *Digestion* 31:168 (1985). Further, it has been reported that divalent heavy metal ions that oxidize or bind to sulfhydryl groups protect animals against ethanol-induced gastric mucosal erosions. Dupuy, D. and Szabo, S., *Gastroenterology* 91:966-977 (1986); Friedman, M., *The Chemistry and Biochemistry of the Sulfhydryl Groups in Amino Acids*, Oxford: Pergamon, 1973, 25-39.

More recently, cytoprotective or gastroprotective drugs are being classified generically as agents with unknown or multiple mechanisms of action. Weinstein, W., *Drug Therapy*, Suppl. 23-27 (1985); Szabo, S., *Gastroenterology* 88:228-236 (1984); Szabo, S., et al., *Gastroenterology* 91:966-974 (1986); Szabo and Bynum, *Scand. J. Gastroenterol.* 23:1-6 (1988). In its most practical and beneficial application, the concept of gastric cytoprotection is directed to the discovery of novel types of antiulcer agents, i.e., drugs that exert gastroprotective or enteroprotective effects by multiple mechanisms of action, without suppressing normal functions such as gastric acid and pepsin secretion. The subject matter of the present invention relates to such drugs.

SUMMARY OF THE INVENTION

The present invention is directed to the treatment of subjects with gastrointestinal ulcer disease by the administration of chemical compounds that provide protection of gastrointestinal mucosa and the mucosal microvasculature.

The invention particularly relates to the use of pyrazole derivatives to treat gastrointestinal ulcer disease. Both ADH inhibitors and ADH non-inhibitors protect against ethanol-induced lesions.

The invention further relates to the preventive treatment of ulcer disease using a pharmaceutical composition consisting of a pyrazole derivative in combination with an agent which is ulcerogenic when administered alone.

The invention further relates to the use of pyrazole derivatives to treat microvascular injury.

DESCRIPTION OF THE PREFERRED EMBODIMENTS

The invention is directed to treatment of ulcer disease in a mammalian subject comprising the administration to said subject of an amount of pyrazole derivative effective to ameliorate, cure, or prevent said ulcer disease. The benefit of said treatment is of long duration.

By the term "pyrazole derivative" is intended pyrazole (a 1,2 diazole) substituted with one or more substituents comprising hydroxy, $C_1$-$C_6$ alkyl, $C_1$-$C_6$ alkyl ethers, aryl, or aralkyl groups. Also intended to be within the scope of pyrazole derivatives are thiazole (sulfur replacing one nitrogen in ring structure) and thiazole derivatives substituted as described for pyrazole.

Typical alkyl groups include methyl, ethyl, propyl, i-propyl, butyl, s-butyl, t-butyl, pentyl, and hexyl.

Typical aryl groups include benzyl, naphthyl, phenyl, pyridinyl, and pyrimidinyl.

The term "pyrazole derivative" also includes pyrazole substituted with one or more halogen substituents, including chlorine, fluorine, bromine and iodine. Pyrazole can be halogenated at a single 3 or 4 position, or can have double halogen substitution at the 3 and 5 positions. The halogen substituents at the 3 and 5 positions can be identical or different.

Preferred derivatives of the present invention are 4-methylpyrazole, 3,5-dimethylpyrazole, 4-iodopyrazole, and thiazole.

By the term "ulcer disease" is intended gastrointestinal injuries in mammals that include, but are not limited to: gastric, duodenal and small intestine ulcer diseases of nonspecific etiology; hemorrhagic and nonhemorrhagic gastric mucosal injuries due to ingestion of alcohol and aspirin-like drugs; gastroduodenal or small intestinal ulcers induced by ingestion of ulcerogenic chemicals and drugs in general; ulcerogenic amine-induced duodenal ulcers such as from cysteamine; alkylnitrile-induced duodenal ulcers such as from propionitrile; duodenal ulcers resulting from ingestion of dopamine antagonists (e.g., haloperidol, pimozide, butaclamol, and flupenthixol); duodenal ulcers resulting from ingestion of dopaminergic neurotoxins (e.g., 1-methyl-4-phenyl-1,2,3,6-tetrahydropyridine and its derivatives and metabolites); duodenal ulcers caused by tyrosine hydroxylase inhibitors (e.g., alpha-methyl-p-tyrosine); gastric ulcers due to suppression of bicarbonate production in the face of increased production of gastric acid and pepsin; and duodenal ulcers due to an improper mix of acid and base in the duodenal bulb.

By the term "ulcerogenic" is meant ulcer-inducing. Ulcerogenic agents such as aspirin, alcohol and cysteamine are discussed above in reference to the meaning of ulcer disease.

By the term "long duration benefit" is meant that the protective effect of a single dose of a pyrazole derivative against gastric erosions and ulcers or alcohol lasts 24–48 hours or longer. The generic gastroprotective agents (e.g. prostaglandins, sulfhydryls) exert an effect for only 3–6 hours.

By the term "treating" is meant the administering to subjects of a pyrazole derivative for purposes which may include prevention, amelioration, or cure of gastrointestinal ulcer disease.

By the term "microvascular injury" is meant damage to blood vessels including capillaries, venules, and arterioles, caused by pathological change in, but not limited to, the vascular endothelium. In one embodiment of this invention, protection from, or therapy of, said ulcer disease results from prevention or amelioration of microvascular injury in blood vessels in the gastric mucosa.

Several animal model systems useful for testing pyrazole derivatives for potential anti-ulcerogenic properties are known to those skilled in the art. Acute gastric cytoprotection is commonly determined in animal models of standard alcohol- or aspirin-induced gastric lesions. Szabo, S., et al., *Gastroenterology* 88:228-236 (1985) and Szabo, S., et al., *J. Pharm. Meth.* 13:59-66 (1985), are hereby incorporated by reference to the extent that these reports disclose methods of creating and using such animal models. Beneficial effects on acute or chronic duodenal ulcers can be assessed in animal models of acute or chronic duodenal ulcers induced by cysteamine. Szabo, S., *Amer. J. Pathol.* 93:273-276 (1978) is herein incorporated by reference to the extent that the report discloses the method and use of such an animal model.

The preferred animal subject of the present invention is a mammal. By the term "mammal" is meant an individual belonging to the class Mammalia. The invention is particularly useful in the treatment of human subjects.

Pyrazole derivatives are tested for cytoprotective effects in vitro by methods well known in the art. Monolayer cell cultures of endothelial cells or suspensions of other cells of the gastric mucosa (e.g., mucous, parietal, chief, and mast cells, Lewin, N. J. M., et al., in Pretlow, T. G., et al., eds., *Cell Separation: Methods and Selected Applications*, Academic Press, New York, 1982, 223-244) are tested for protection against ulcerogenic substances (e.g., alcohol, hydrochloric acid, aspirin), by the addition of a pyrazole derivative to said cell cultures or suspensions. Cell viability is determined by standard methods, such as the exclusion of vital dyes (e.g. Trypan blue, ethidium bromide), assessed using light or fluorescence microscopy, respectively.

The pharmaceutical composition of the present invention may be, comprised of a pyrazole derivative in combination with an ulcerogenic agent. Medicaments are considered to be provided "in combination" with one another if they are provided to the patient concurrently, or if the time between the administration of each medicament is such as to permit an overlap of biological activity. In one preferred embodiment, the pyrazole derivative and an ulcerogenic agent comprise a single pharmaceutical composition.

By the administering of a pyrazole derivative in combination with an ulcerogenic therapeutic agent, one may ameliorate or prevent the ulcerogenic effect of said agent.

The pharmaceutical compositions of the present invention wherein pyrazole derivatives are combined with an ulcerogenic agent may be administered by any means that achieve their intended purpose. Amounts and regimens for the administration of pyrazole derivatives can be determined readily by those with ordinary skill in the clinical art of treating gastrointestinal ulcer disease. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

Compositions within the scope of this invention include all compositions wherein the pyrazole derivative is contained in an amount effective to achieve its intended purpose. While individual needs vary, determination of optimal ranges of effective amounts of each component is within the skill of the art. Typical dosages comprise 0.1 to 100 mg/kg/body wt. The preferred dosages comprise 1 to 100 mg/kg/body wt. The most preferred dosages comprise 10 to 100 mg/kg/body wt.

In addition to the pharmacologically active compounds, the new pharmaceutical preparations may contain suitable pharmaceutically acceptable carriers comprising excipients and auxiliaries which facilitate processing of the active compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 20 to 75 percent of active compound(s), together with the excipient.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example, lactose or sucrose, mannitol or sorbitol, cellulose preparations and/or calcium phosphates, for example, tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethylstarch, cross-linked polyvinyl pyrrolidone, agar, or alginic acid or a salt thereof, such as sodium alginate.

Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose, phthalate are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The pushfit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils or liquid paraffin. In addition, stabilizers may be added.

Possible pharmaceutical preparations which can be used rectally include, for example, suppositories which consist of a combination of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides. Aqueous injection suspensions that may contain substances which increase the viscosity of the suspension include, for example, sodium carboxymethyl cellulose, sorbitol, and/or dextran. Optionally, the suspension may also contain stabilizers.

EXAMPLES

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

All the studies in the following examples were performed in Sprague-Dawley rats with initial body weights of 150-200 g. The animals were given Purina lab chow and tap water ad lib, but were fasted 24 hr before the experiment. Each group consisted of 3 rats, and each experiment was repeated at least twice. Results were pooled, yielding 6-9 rats per treatment group.

EXAMPLE 1

4-methylpyrazole and 4-iodopyrazole, inhibitors of ADH, and 3,5-dimethylpyrazole, a non-inhibitor of ADH, were tested for prevention of hemorrhagic gastric erosions. Fasted animals received the designated dose 4-methylpyrazole, 3,5-dimethylpyrazole, or 4-iodopyrazole, 30 min. before administration of 1 ml 100% ethanol by gavage. Animals were sacrificed 1 hr. after ethanol treatment and the extent of hemorrhagic gastric mucosal lesions were measured by computerized planimetry. Results are expressed as percent of the glandular stomach mucosa which is damaged. The extent of the lesions and the degree of protection were also verified by histology and light microscopy of standard sections of the stomach.

4-methylpyrazole produced highly significant ($p<0.05$) dose-related decreases in gastric erosion (see Table 1.)

TABLE 1

PYRAZOLE COMPOUNDS PROTECT AGAINST ETHANOL-INDUCED GASTRIC EROSIONS
AREA OF EROSION (% of Glandular Stomach)

| Drug Dose (mg/kg) | 4-methyl-pyrazole | 4-iodopyrazole | 3,5-dimethylpyrazole |
|---|---|---|---|
| 0. | 26.1 | 26.1 | 26.1 |
| 50. | 8.5 | — | — |
| 100. | 0.2 | — | — |
| 250. | — | — | — |
| 500. | 0.5 | 3.7 | 0 |

The ADH non-inhibitor 3,5-dimethylpyrazole, at doses of 500 mg/kg body weight, completely abolished hemorrhagic lesions 1 hr after ethanol administration. An additional ADH inhibitor, 4-iodopyrazole, decreased damage to 3.7% of the glandular stomach in doses of 500 mg/kg body weight 1 hour after ethanol administration. It is concluded that both ADH inhibitor and non-inhibitor derivatives of pyrazole exert potent gastroprotective effects against ethanol-induced hemorrhagic gastric erosions.

EXAMPLE 2

In order to demonstrate that gastroprotection by pyrazole derivatives is not limited to alcohol-induced injury, additional agents capable of inducing gastric lesions, such as hydrochloric acid and aspirin, were tested. Here, 500 mg/kg 3-methylpyrazole was administered per os either 0.5, 24, or 48 hr prior to treatment by gavage with either 0.6 N HCl or 100 mg/kg aspirin. Rats were sacrificed 1 hr after this treatment and gastric damage evaluated.

3-methylpyrazole offered virtually complete protection against acid-induced damage. Aspirin induced damage to 2.1% of the mucosa. 3-methylpyrazole given at 0.5 hr. and 24 hr earlier reduced the damage to 0% and 1.2%, respectively. It is concluded that pyrazole derivatives are effective against gastric lesions induced by acid and aspirin and that this effect is also of long duration (about 24 hr).

EXAMPLE 3

Rats were treated with thiazole in order to determine whether replacement of a nitrogen group with sulfur affected gastroprotective activity. Thiazole, 50 mg/kg per os, was administered 30 min before ethanol administration as above. Animals were examined 1 hr after ethanol gavage. Control groups given ethanol alone showed damaged mucosa involving 16% of glandular stomach. This was significantly ($p<0.005$) reduced to 3.9% by pretreatment with thiazole. It is concluded that a derivative of pyrazole, in which one of the two nitrogents is replaced by sulfur, exhibits gastroprotective properties.

We claim:

1. A method for treating gastrointestinal ulcer disease in mammals, comprising:
   administering to a mammal in need of such treatment a gastroprotective agent in an amount effective to treat said gastrointestinal ulcer disease, said gastroprotective agent comprising:
   1,2-diazole substituted with one or more members selected from the group consisting of hydroxy, $C_1$–$C_6$ alkyl ether, aryl, and aralkyl, or
   substituted or unsubstituted thiazole, wherein said substituted thiazole is substituted with one or more members selected from the group consisting of: hydroxy, $C_1$–$C_6$ alkyl, $C_1$–$C_6$ alkyl ether, aryl, aralkyl, and halogen.

2. The method of claim 1, wherein said treating comprises prevention of gastrointestinal ulcer disease.

3. The method of claim 1, wherein said treating comprises amelioration of gastrointestinal ulcer disease.

4. The method of claim 1, wherein said treating comprises the cure of gastrointestinal ulcer disease.

5. The method of claim 1, wherein said ulcer disease is gastric.

6. The method of claim 1, wherein said ulcer disease is duodenal.

7. The method of claim 1, wherein said ulcer disease is in the small intestine.

8. The method of claim 1, wherein said mammals are humans.

9. The method of claim 1, wherein said gastroprotective agent is administered orally, subcutaneously, nasally, rectally, intravenously or transdermally.

10. The method of claim 1, wherein said effective amount is a dosage in the range 0.1 to 100 mg/kg.

11. The method of claim 1, wherein said gastroprotective agent is thiazole.

12. A method for preventing the ulcerogenic effect of a therapeutic agent, comprising:
   administering a combination of said therapeutic agent and a gastroprotective agent, in an amount effective to prevent the ulcerogenic effect of said therapeutic agent, to a subject receiving said therapeutic agent, said gastroprotective agent comprising:
   1,2-diazole substituted with one or more members selected from the group consisting of hydroxy, $C_1$–$C_6$ alkyl ether, aryl, and aralkyl, or
   substituted or unsubstituted thiazole, wherein said substituted thiazole is substituted with one or more members selected from the group consisting of: hydroxy, $C_1$–$C_6$ alkyl, $C_1$–$C_6$ alkyl ether, aryl, aralkyl, and halogen.

13. The method of claim 12, wherein said therapeutic agent is selected from the group consisting of aspirin, indomethacin, naproxen, ibuprofen, phenylbutazone, glucocorticods, and other steriodal and non-steroidal anti-inflammatory drugs.

14. The method of claim 12, wherein said gastroprotective agent is thiazole.

15. The method of claim 12, wherein said gastroprotective agent is administered orally, subcutaneously, nasally, rectally, intravenously or transdermally.

16. The method of claim 12, wherein said effective amount is a dosage in the range of 0.1 to 100 mg/kg.

17. A method for treating microvascular injury in mammals, comprising:
   administering to a mammal in need of such treatment a gastroprotective agent in an amount effective to treat said microvascular injury, said gastroprotective agent comprising:
   1,2-diazole substituted with one or more members selected from the group consisting of hydroxy, $C_1$–$C_6$ alkyl ether, aryl, and aralkyl, or substituted or unsubstituted thiazole, wherein said substituted thiazole is substituted with one or more members selected from the group consisting of: hydroxy, $C_1$-$C_6$ alkyl, $C_1$-$C_6$ alkyl ether, aryl, aralkyl, and halogen.

18. The method of claim 17 wherein said treating comprises prevention of microvascular injury.

19. The method of claim 17, wherein said treating comprises amelioration of microvascular injury.

20. The method of claim 17, wherein said treating comprises the cure of microvascular injury.

21. The method of claim 17, wherein said mammals are humans.

22. The method of claim 17, wherein said gastroprotective agent is administered orally, subcutaneously, nasally, rectally, intravenously or transdermally.

23. The method of claim 17, wherein said effective amount is a dosage in the range 0.1 to 100 mg/kg.

24. The method of claim 17, wherein said gastroprotective agent is thiazole.

25. The method of any one of claims 1, 12 or 17 wherein said $C_1$-$C_6$ alkyl member is selected from the group consisting of: methyl, ethyl, propyl, i-propyl, butyl, s-butyl, t-butyl, pentyl, and hexyl, and said aryl member is selected from the group consisting of benzyl, napthyl, phenyl, pyridinyl and pyrimidinyl.

26. The method of any one of claims 1, 12 or 17, wherein said gastroprotective agent does not suppress gastric acid secretion.

27. The method of any one of claims 1, 12, or 17 wherein said substituted thiazole contains one or more halogen substituents.

28. The method of claim 27 wherein said halogen substituent is chosen from the group consisting of chlorine, bromine, iodine and fluorine.

29. A pharmaceutical composition, comprising:
a gastroprotective agent in combination with an ulcerogenic therapeutic agent, said gastroprotective agent comprising:
1,2-diazole substituted with one or more members selected from the group consisting of hydroxy, $C_1$-$C_6$ alkyl ether, aryl, and aralkyl, or
substituted or unsubstituted thiazole, wherein said substituted thiazole is substituted with one or more members selected from the group consisting of: hydroxy, $C_1$-$C_6$ alkyl, $C_1$-$C_6$ alkyl ether, aryl, aralkyl, and halogen.

30. The pharmaceutical composition of claim 29, wherein said therapeutic agent is selected from the group consisting of aspirin, indomethacin, naproxen, ibuprofen, phenylbutazone, glucocorticoids, and other steriodal and non-steroidal anti-inflammatory drugs.

31. The pharmaceutical composition of claim 29, wherein said therapeutic agent is thiazole.

32. The pharmaceutical composition of claim 29 wherein said substituted thiazole contains one or more halogen substituent(s).

33. The pharmaceutical composition of claim 32 wherein said halogen substituent is chosen from the groups consisting of chlorine, bromine, iodine and fluorine.

34. The pharmaceutical composition of claim 29, wherein said $C_1$-$C_6$ alkyl member is selected from the group consisting of: methyl, ethyl, propyl, i-propyl, butyl, s-butyl, t-butyl, pentyl, and hexyl, and said aryl member is selected from the group consisting of benzyl, napthyl, phenyl, pyridinyl and pyrimidinyl.

35. The pharmaceutical composition of claim 29, wherein said gastroprotective agent does not suppress gastric acid secretion.

* * * * *